(12) United States Patent
Wang et al.

(10) Patent No.: US 8,021,625 B2
(45) Date of Patent: Sep. 20, 2011

(54) INTERRUPTED, GRAVITY-PROMOTED, DIFFUSED FLOW CHROMATOGRAPHY STRIP TESTING DEVICE AND METHOD

(75) Inventors: Naishu Wang, San Diego, CA (US); David F. Zhou, San Diego, CA (US)

(73) Assignee: DNT Scientific Research, LLC, San Diego, CA (US)

( * ) Notice: Subject to any disclaimer, the term of this patent is extended or adjusted under 35 U.S.C. 154(b) by 276 days.

(21) Appl. No.: 11/881,455

(22) Filed: Jul. 27, 2007

(65) Prior Publication Data

US 2007/0269906 A1 Nov. 22, 2007

Related U.S. Application Data

(60) Continuation-in-part of application No. PCT/US2006/003018, filed on Jan. 27, 2006, and a continuation-in-part of application No. 11/738,356, filed on Apr. 20, 2007, now Pat. No. 7,655,184, which is a division of application No. 11/258,636, filed on Oct. 26, 2005, now Pat. No. 7,238,322, which is a continuation-in-part of application No. 11/090,463, filed on Mar. 25, 2005, now Pat. No. 7,638,093, which is a continuation-in-part of application No. 10/767,897, filed on Jan. 28, 2004, now abandoned.

(51) Int. Cl.
*G01N 31/22* (2006.01)

(52) U.S. Cl. ........... 422/414; 422/50; 422/63; 422/68.1; 422/82.05; 422/82.06; 422/110; 422/412; 435/286.6; 435/287.1; 435/287.3; 435/287.6; 435/288.4; 435/288.5; 436/52; 436/53; 436/54; 436/165; 436/180

(58) Field of Classification Search ............... 422/50, 422/55, 63, 68.1, 82.05, 82.08, 100, 110, 422/412, 414; 435/286.6, 287.1, 287.3, 287.6, 435/288.4, 288.5; 436/52, 53, 54, 165, 180
See application file for complete search history.

(56) References Cited

U.S. PATENT DOCUMENTS

| | | | | |
|---|---|---|---|---|
| 6,300,142 B1 * | 10/2001 | Andrewes et al. | ............ | 436/518 |
| 6,663,833 B1 * | 12/2003 | Stave et al. | ............ | 422/81 |
| 6,890,484 B2 * | 5/2005 | Bautista et al. | ............ | 422/58 |
| 7,238,322 B2 | 7/2007 | Wang et al. | | |
| 2005/0112023 A1 * | 5/2005 | Liang | ............ | 422/58 |
| 2005/0153271 A1 * | 7/2005 | Wenrich | ............ | 435/1.1 |
| 2005/0164404 A1 * | 7/2005 | Marlborugh et al. | ............ | 436/514 |
| 2005/0186111 A1 * | 8/2005 | Wang et al. | ............ | 422/56 |
| 2007/0184492 A1 * | 8/2007 | Wang et al. | ............ | 435/7.1 |

* cited by examiner

*Primary Examiner* — Gail R Gabel
(74) *Attorney, Agent, or Firm* — Charmasson Buchaca & Leach, LLP

(57) ABSTRACT

A device and method for enhancing rapid confirmatory immunological testing ("RCIT") in chromatography strip-type rapid IVD devices useful in, for example, clinical, point-of-care, laboratory or over-the-counter settings. The device drives a flow fluid, primarily under the force of gravity alone, through a first chamber having a porous dam structure to enhance and substantially complete the first affinity binding reaction between a source of mobilizable labeled binding members and an analyte in the fluid. Flow through the dam causes a delay, mixing and trapping of the typically chemically disuniform initial fluid front so that fluid exiting the dam exhibits a more uniformly high degree of first affinity binding and decreased non-affinity binding. Afterward, and without further human interaction, the fluid then flows under the combined, turbulence creating forces of gravity, siphoning, and capillarity, through a second chamber containing a chromatographic strip which captures the labeled analytes in a second affinity binding reaction. By separating the two affinity binding reactions, competition for analytes during each reaction is reduced, and thus accuracy improved.

20 Claims, 5 Drawing Sheets

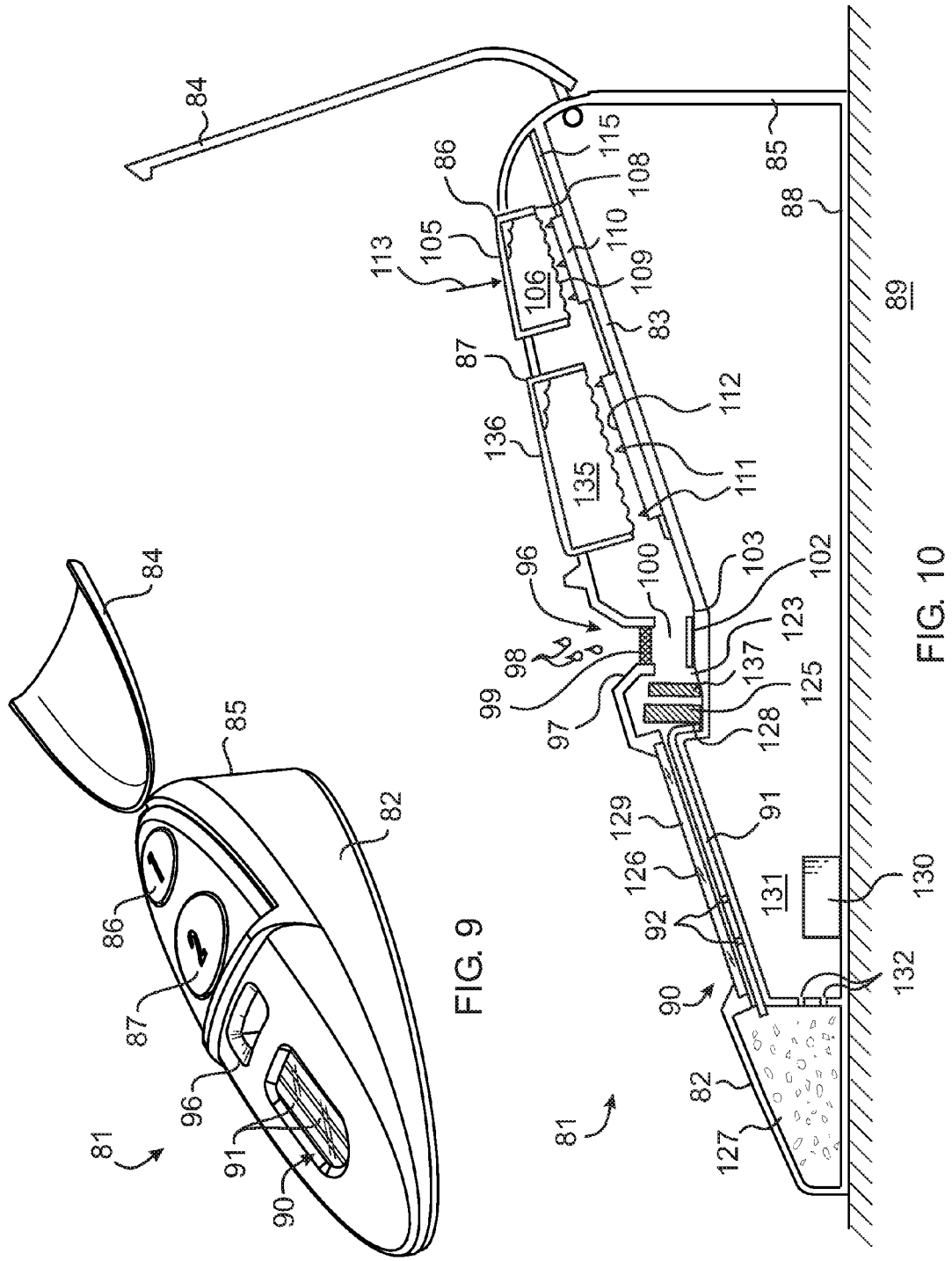

INTERRUPTED, GRAVITY-PROMOTED, DIFFUSED FLOW CHROMATOGRAPHY STRIP TESTING DEVICE AND METHOD

PRIOR APPLICATION

This application is a continuation-in-part of International patent application No. PCT/US06/03018 filed 27 Jan. 2006 designating the U.S. This application is also a continuation-in-part of U.S. patent application Ser. No. 11/738,356 filed 20 Apr. 2007, now U.S. Pat. No. 7,655,184 issued 2 Feb. 2010, which is a divisional of U.S. patent application Ser. No. 11/258,636 filed 26 Oct. 2005 now U.S. Pat. No. 7,238,322 which is a continuation-in-part of U.S. patent application Ser. No. 11/090,463 filed Mar. 25, 2005, now U.S. Pat. No. 7,638,093 issued 29 Dec. 2009, which is a continuation-in-part of U.S. patent application Ser. No. 10/767,897 filed Jan. 28, 2004 abandoned.

FIELD OF THE INVENTION

This invention relates to apparatuses for analyzing fluids such as body fluids using immunochromatography, and more particularly to chromatographic strip test apparatuses for detecting analytes such as antibodies or antigens which may indicate a particular condition in a clinical, point-of-care or large-scale laboratory setting, or in the over-the-counter, home-use setting.

BACKGROUND

Over past decades, the prior art has offered several types of rapid diagnostic testing techniques which use a body fluid such as whole blood, serum, plasma, urine, spinal fluid, amniotic fluid, mucous, saliva, and the like for detecting the presence of infection or other conditions such as cancer, pregnancy, abused drugs and cardiovascular disorders such as acute myocardial infarction (AMI). Such tests are often referred to collectively as rapid In Vitro Diagnostic ("IVD") device tests.

Unfortunately, prior rapid IVD test devices are typically useful only for preliminary screening purposes, not as a confirmatory test. Although they can be fast, inexpensive, and simple-to-use, depending on the type of condition being detected, these tests provide a typical accuracy of between 85% and 99%, falling short of the 99.9% or above accuracy generally considered to be necessary for a confirmatory test. To this day, for example, the Western Blot Analytical Assay is the only one reliably used for the confirmatory detection of HIV infection in a clinical laboratory setting worldwide. Due to its multi-step manipulation and verification phases, completion of this type of test can take days, if not weeks. Such a delay can unfortunately lead to further propagation of infectious pathogens such as HIV. Other serious results, such as the metastasis of cancers, can occur while waiting for the results of slower confirmatory tests. There is virtually no generally accepted practical or economical confirmatory rapid diagnostic testing technique for use in a point-of-care setting to rapidly detect serious diseases such as HIV infection and AMI, available in the market place today.

The reasons for the insufficient accuracy in many rapid IVD test devices are primarily due to their current lack of overall higher sensitivity and specificity. Different samples may contain chemicals or particles which inhibit the fluid flow or otherwise interfere with one or both of the affinity binding reactions. Prior devices have attempted to enhance sensitivity or specificity by pretreating various parts of the device with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially on the reaction membrane. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Or, the manufacturing step of pretreating with the second pretreatment chemical can dislodge some of the first pretreatment chemical.

Further, lot-to-lot variation in the manufacture of many IVD test devices can often lead to ambiguous results, such as false negatives as well as weak false positives, so-called "ghost lines" or "phantom lines". False negatives typically occur when non-specific molecules interfere with the first and/or second affinity binding actions. It has been found that non-analyte molecules can clump together in fluid samples that are not well mixed so that they temporarily prevent access between analytes and binding members. Even temporary interference can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive.

Chemically non-uniform flows can result in flows having non-uniform first affinity binding by the time they reach the reaction membrane leading to inaccuracies. Such non-uniform flows can be caused by a number of factors. First, some portions of the fluid may flow faster than others from time to time. In those tests having deposits of dried reagent, faster flows tend to reach the dried reagent first. These flows, particularly along the initial fluid front, tend to exhibit a greater degree of first affinity binding per unit fluid or at least uptake of mobilizable labeled binding members, and can potentially carry a greater concentration of clumps of non-analyte molecules which can carry away labeled mobilized binding members. Further, the deposit of dried reagent itself can exhibit portions of higher concentration than others resulting in similar chemical nonuniformity in the flow. Other flows having a lower than average concentration of analyte molecules, and/or having a greater concentration of non-clumped, non-analyte molecules which merely inhibit analyte binding but do not carry away mobilizable labeled binding members, exhibit less apparent first affinity binding. These flow and concentration dis-uniformities are responsible for many of the unsatisfactory results discussed above.

Therefore, there is a need to improve the accuracy of rapid IVD test devices so that Rapid Confirmatory Immunological Testing ("RCIT") becomes a reality.

SUMMARY

The instant embodiments provide a more advanced way of rapidly confirming the presence of cancer, infection or other conditions such as pregnancy, cardiovascular disorders, and abused drugs in body fluids through the use of directed fluid flow-based chromatographic immunoassay test devices and thus potentially avoid the long turn-around time required by separate assays using multiple test procedures such as in a Western Blot assay.

The instant embodiments provide an improvement for flow-based immunological strip testing devices for rapidly conducting a confirmatory immunoassay. These instant embodiments may also provide rapid IVD devices that can be used, for example, in a clinical, professional, point-of-care setting, in a laboratory setting or in an over-the-counter, home-use setting.

Some of the instant embodiments provide a porous, flow delaying, flow-diffusing and intitial fluid front trapping structure interposed on a downward flowing fluid path between a source of a labeled mobilizable binding member and a reaction membrane. That flow is directed by various structures and force interactions as will be explained below. The diffusive structure causes numerous fluid furcations and convergences, and diversion and trapping of the typically chemically disuniform initial fluid front to improve fluid mixing and uniformity causing a more uniformly high degree of first affinity binding before crossing into the reaction membrane. Once in the membrane, the combined forces of gravity, siphoning and capillarity, further mix and disperse the flow, enhancing the quality of the second affinity binding. Both increase the sensitivity and specificity (accuracy) of the device, and constitutes an advancement in performance over prior rapid IVD test devices.

In some embodiments there is provided a flow immunoassay device for testing a fluid specimen for the presence of an analyte, wherein said device comprises: a first chamber shaped and dimensioned to accept said specimen and be subjectable to a source of a mobilizable labeled binding member bindable to said analyte; a second chamber holding at least one test result signal generator responsive to an amount of said analyte bound to said labeled binding member; a flow interrupting formation located on a fluid path between said first and second chambers; wherein said fluid flows to said flow interrupting structure primarily under the force of gravity alone; wherein said fluid flows through said generator primarily under the combined forces of gravity, siphoning and capillarity; and, whereby a first affinity binding reaction between said analyte and said labeled binding member is substantially completed before said fluid enters said second chamber.

In some embodiments, said formation comprises: a first porous diffusive structure. In some embodiments, said first structure has a first pretreatment condition. In some embodiments, said first pretreatment condition is selected from the group consisting of: being pretreated with a surfactant; being pretreated with a pH conditioner, being pretreated with a non-specific adhesive blocking molecule, and having no pretreatment. In some embodiments, said device further comprises a second mixing, diffusing and filtering structure, wherein said first structure has a first pretreatment condition and said second structure has a second pretreatment condition, and wherein said first pretreatment condition is different from said second pretreatment condition. In some embodiments, said first structure is shaped and dimensioned to have a trap portion at an elevation higher than fluid entry and exit portions. In some embodiments, said first structure comprises a material selected from the group consisting of: glass fiber, cellulose and fibrous plastic and the like. In some embodiments, there is no direct fluid flow contact between said source and said generator without passing through said first formation. In some embodiments, said first structure comprises means for diverting an initial fluid front passing therethrough. In some embodiments, said device further comprises: said structure comprising a first material having a plurality of fibers oriented substantially differently to one another and branching into furcations and convergences. In some embodiments, said generator comprises a chromatographic test strip including a reaction membrane oriented in an oblique, downward flow orientation, said membrane having at least one test zone. In some embodiments, said strip is formed without a source of mobilizable labeled binding members. In some embodiments, said generator comprises a plurality of test zones adapted to provide a measurable basis for a quantitative result display. In some embodiments, the device further comprises means for dispensing said supply into said first chamber. In some embodiments, said device is formed in absence of a pump built into said device. In some embodiments, the device further comprises a user manipulatable dispenser shaped and dimensioned to releasably hold a supply of a mix buffer solution, wherein said dispenser in an open condition is in fluid communication with said first formation. In some embodiments, said supply of mix buffer solution has a volume between about 200 microliters and about 300 microliters. In some embodiments, the device further comprises a second supply of wash buffer solution having a volume between about 2.5 milliliters and about 3 milliliters. In some embodiments, said formation comprises a flow delaying reservoir separated into first and second zones by a first porous structure. In some embodiments, a second affinity binding reaction occurs in absence of any substantial continuation of said first affinity binding reaction.

In some embodiments, there is provided a method for conducting a fluid flow immunoassay for at least one analyte, wherein said method comprises: diffusing a fluid mixture comprising a specimen containing an analyte, a mix buffer and a mobilizable labeled binding member bindable to said analyte through a diffusive structure before said mixture reaches at least one reaction membrane having a capture binding member bindable to said analyte.

In some embodiments, the method further comprises moving said mixture along a surface of said membrane under the combined forces of gravity, siphoning and capillary. In some embodiments, the method further comprises pretreating said diffusive structure with a surfactant. In some embodiments, the method further comprises substantially completing a first affinity binding reaction between said mobilizable labeled binding member and said analyte at a location and time apart from a second affinity binding reaction between said analyte and said capture binding member.

BRIEF DESCRIPTION OF THE DRAWINGS

FIG. 9 is a perspective view of an embodiment of the interrupted, gravity promoted, downward flow testing device having programmed dispensing of mix and wash buffers.

FIG. 10 is a diagrammatical cross-sectional side view of the device of FIG. 9.

DESCRIPTION OF THE EXEMPLARY EMBODIMENTS

Figure 1:
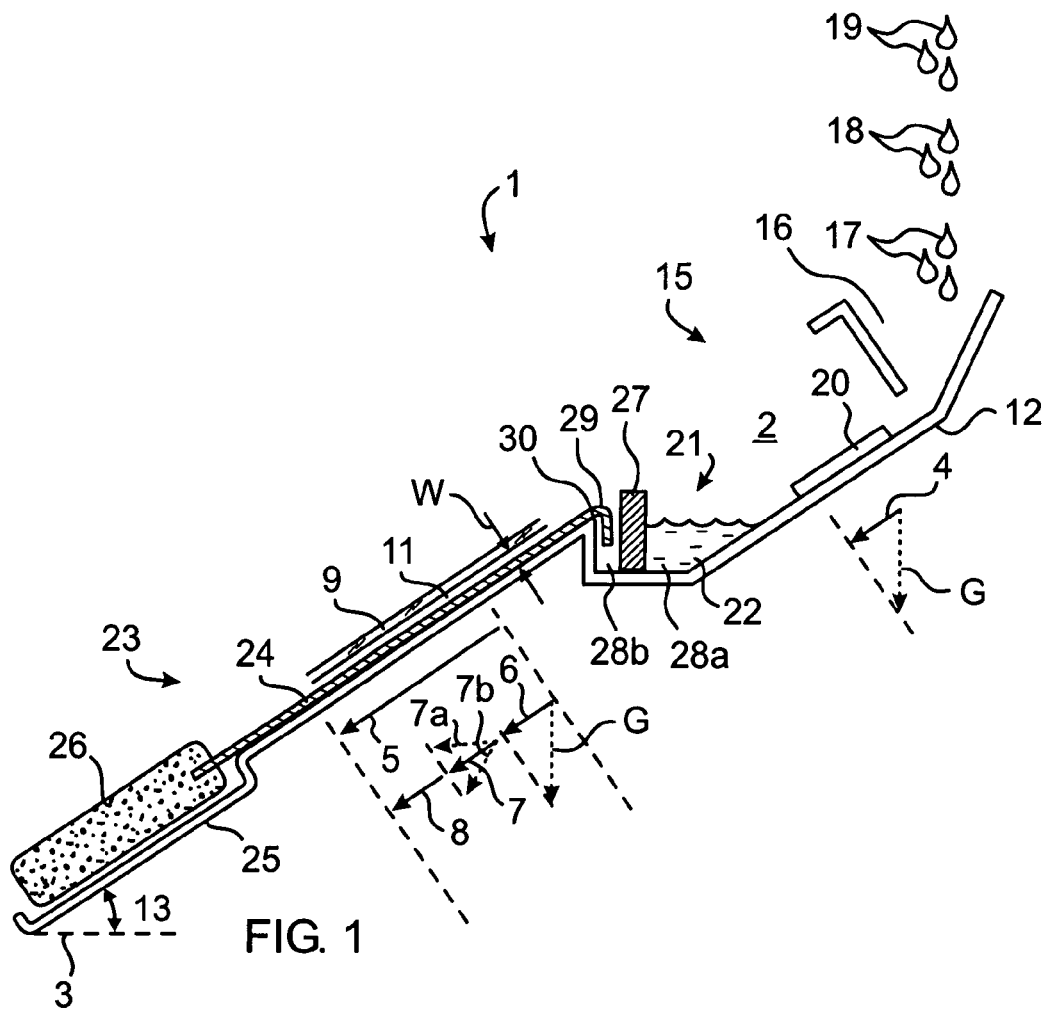
FIG. 1 is a diagrammatical cross-sectional illustration of an interrupted, gravity assisted flow testing device and a schematic representation of the fluid flow driving forces.

The instant devices are useful to rapidly and confirmatorily determine the presence of analyte in a sample or specimen as disclosed in our U.S. Pat. No. 7,238,322 (Wang et al.) incorporated herein by this reference. The sample can include, for example, body fluids such as whole blood, serum, plasma, urine, spinal fluid, amniotic fluid, mucous, saliva, and the like, or other fluids used in certain food and environmental testing.

Analyte, as used herein, refers to a compound or composition to be measured. The analyte can be any substance (antigen or ligand) for which there exists a naturally or genetically occurring specific binding member such as a binding molecule (e.g., an antibody or receptor and the like) and other molecules that exhibit the so-called "lock-in-key" pairing function.

Analyte also includes any antigenic substances, haptens, antibodies, and combinations thereof. The analyte can include a protein, a peptide, an amino acid, a ligand, a hormone, a steroid, a vitamin, a drug including those administered for therapeutic purposes as well as those administered for illicit purposes, a pathogen, and an exogenious infectious microbe such as a bacterium, a virus, and metabolites of or antibodies to any of the above substances. The analyte can also comprise an antigenic marker or antibody or receptor for single or multiple pathogenic conditions.

The precise nature of a number of analytes together with a number of examples thereof are disclosed in Litman, et al., U.S. Pat. No. 4,299,916, issued Nov. 10, 1981; and Tom, et al., U.S. Pat. No. 4,366,241, issued Dec. 28, 1982, each of which is hereby incorporated by reference in its entirety.

The signal provided to the user of the device is provided by accumulation of a visually detectable label conjugated to a mobilizable binding member such as a specific antibody and/or antigen; ligand and/or receptor. This mobilizable binding member is sometimes referred to as a "binding member molecule", "a first affinity binding member", "labeled binding member" or simply "conjugate". In the instant embodiments, labels that produce a readily detectable signal are used. Thus, the instant embodiments provide colored labels which permit visible detection of the assay results without the addition of further substances and/or without the aid of instrumentation.

Examples of labels that can readily detected include, for example, colloidal gold, colloidal carbon, latex beads, magnetic beads, and the like, and which can more generally be characterized as dye sols, metal sols, nonmetal sols, colored latex particles, color indicators, colored matter encapsulated in liposomes, and the like.

Metal sols are disclosed in Leuvering, U.S. Pat. No. 4,313,734, issued Feb. 2, 1982 and Moeremans, et al., U.S. Pat. No. 4,775,636, issued Oct. 4, 1988, each of which is hereby incorporated by reference in its entirety, and comprise a metal, a metal compound, such as metal oxides, metal hydroxides and metal salts, or polymer nuclei coated with metal or metal compound. The metal sols can comprise, for example, metals such as platinum, gold, silver and copper. Alternatively, or additionally, the metal sols can comprise metal compounds, such as, for example, silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate and titanium dioxide.

Nonmetal sols, such as carbon sols and their use are described in Kang, et al., U.S. Pat. No. 5,559,041, issued Sep. 24, 1996, which is hereby incorporated by reference in its entirety. Nonmetal colloidal particles, such as selenium particles, are disclosed in Yost, et al., U.S. Pat. No. 4,954,452, issued Sep. 4, 1990, which is hereby incorporated by reference in its entirety. Other nonmetals that can be used include elements within Group VIB. of the Periodic Table, such as sulfur, and tellurium.

Labels can also be formed from dye polymers, whereby dye molecules, or chromogenic monomers, are polymerized to form a colored polymer particle. Examples of such dyes include Congo red, Trypan blue, and Lissamine blue.

Organic polymer latex particles are disclosed in Tarcha, et al., U.S. Pat. No. 5,252,459, issued Oct. 12, 1993, which is hereby incorporated by reference in its entirety. Such particles can comprise a plurality of non-chromophoric monomers.

Particulate labels comprising a dye or other colored substance enclosed in liposome sacs are described in Campbell, et al., U.S. Pat. No. 4,703,017, issued Oct. 27, 1987; and Rosenstein, U.S. Pat. No. 5,591,645, issued Jan. 7, 1997, each of which is hereby incorporated by reference in its entirety.

The devices described in these embodiments use test strips, dams and/or pads that can comprise a dry porous material. By "porous" it is meant that the matrix is composed of a material into which fluids can flow and can pass through. Representative materials include nylon, plastic, fiber containing paper, such as filter paper, chromatographic paper, and the like, nitrocellulose, glass fibers, polysulfone, polyvinylidene difluoride, polyurethane, and other porous polymers, polysaccharides, (e.g., cellulose materials, such as paper and cellulose acetate), silica, inorganic materials, such as deactivated alumina, diatomaceous earth, $MgSO_4$, or other inorganic finely divided material conveniently substantially uniformly dispersed in a porous polymer matrix, with polymers such as vinyl chloride, vinyl chloride-propylene copolymer, and vinyl chloride-vinyl acetate copolymer; cloth, both naturally occurring e.g., cotton and synthetic, (e.g., nylon cloth), porous gels, (e.g., silica gel, agarose, dextran, and gelatin), polymeric films, (e.g., polyacrylamide), and the like. In exemplary embodiments, the test strips comprise POREX CHEMISTRY A and/or POREX CHEMISTRY K membranes commercially available from Porex Corporation, Fairburn, Ga., and/or NOVYLON brand membrane commercially available from Cuno Incorporated, Meriden, Conn.

The exemplary embodiments will be described in connection with the detection of HIV in a fluid specimen as a putative target analyte. Those skilled in the art will readily appreciate adaptation of these embodiments to detect other analytes indicative of other pathogens, or pathogenic conditions in body, food or environmental fluid samples.

Referring now to the drawing, there is shown in FIG. 1a diagrammatical illustration of a rapid IVD immunoassay device 1 having a generally inclined orientation angle 13 to the horizon 3 to direct the flow of fluids throughout the device in absence of any pumps, and a schematic representation of the various fluid flow driving forces. In the upper region 15 of the device a platform 12 partially defines a first chamber 2 and supports a well 16 for accepting a fluid specimen 17 which is combined with a supply of aqueous mix buffering solution 18. The combined fluids contact a porous conjugate pad 20 located beneath the filter and impregnated with a lyophized, mobilizable, first affinity binding member such as an HIV antigen or antibody, conjugated to a label such as colloidal gold. Alternately, the mix buffer solution can be preformulated to carry an amount of first affinity binding members in suspension.

The oblique orientation of the platform 12 creates an oblique force component 4 derived from primarily the force of gravity alone G which drives the combined fluid toward a reservoir or pit 21 formed at the base of the first chamber where a volume 22 of the combined fluid temporarily accumulates. The pit therefore acts as a flow interrupting formation which allows time for the first affinity binding reaction to substantially completely occur. A porous dam 27 divides the pit 21 into an upstream zone 28a and downstream zone 28b. The combined fluid passes through the dam from the upstream to the downstream zone. The diffusive, filtering and initial fluid front diverting function of the dam, which will be described in greater detail below, further enhances the first affinity binding reaction. The term "substantially" is used because some small amount, such as less than 2%, of the first affinity binding reaction may continue to occur after the fluid leaves the pit.

In the lower region 23 of the device, the slanted platform 12 partially defines a second chamber 11 behind a transparent viewing window 9 for holding a test result signal generator having at least one down-flow chromatographic strip 24 having a reaction membrane coated with an immoblized, capture, second affinity binding member. The upper edge 29 of the strip 24 is bent to dip into the downstream zone 28b of the pit over an escape port 30. An oblique force 5 combining gravity, capillary, and siphoning forces drives the combined fluid through the second chamber 11.

After a predetermined time, an amount of wash buffer 19 is deposited into the well 16 to flush through the chambers 2,11. At the bottom 25 of the device, the down-flow strip 24 is in contact with an absorbing pad 26 which encourages siphoning through the strip. The size of the absorbing pad is selected to accommodate all of the fluids used in the device.

As shown schematically in FIG. 1, the oblique force 5 is derived from the summation of: 1) a gravity force component 6 derived from the orientation the platform 12 in the second chamber 11; 2) a capillary force component 7 derived from the narrow width W of the second chamber, which can be less than 5 millimeters and typically less than about 3 millimeters, which creates capillary forces 7a,7b; and, 3) a siphoning force component 8 caused by the second chamber being substantially filled with fluid and the sucking force action of the absorbing pad 26. It should be noted that the capillary, siphoning and gravity forces combine from different directions in the second chamber to drive the fluid flow down along the membrane in a more turbulent way, creating a more uniform mixture, and thus enhancing second affinity binding.

It should also be noted that by separating the first and second affinity binding reactions in both time and location, the competition for analytes during each reaction is significantly reduced thereby increasing accuracy.

The strips are held in an inclined rather than straight vertical position in order to reduce the height of the device yet still provide a gravitational force component in the direction of the fluid flow and discourage reverse flow of fluid back up into the strips—a common problem with flow-through devices. In this way, there is no uninterrupted fluid flow contact between the conjugate source and the reaction membrane, but rather the fluid must pass through the diffusive dam before reaching the reaction membrane.

The device is particularly characterized by its reliance on: 1) the separation between the conjugate source and the reaction membrane to allow for substantially all of the first affinity binding to occur prior to the fluid reaching the strips or strips; 2) the flow-delaying and incubative properties of the pit 21 interposed between the conjugate source and reaction membrane; 3) the automatic mechanical and chemical mixing, diffusing, filtering and initial fluid front diverting and trapping functions of the dam 27; and, 4) the use of gravity alone in the upper part of the device and the combination of gravity, siphoning and capillary forces driving flow in the reaction membrane, to allow a low human interaction, gravity-driven downward fluid flow device without active pumping mechanisms.

The down-flow type strip used in the device differs from common chromatographic strips typically used in lateral flow tests in that it does not have a conjugate pad and is therefore without a source of mobilizable, labeled binding members. Each down-flow strip does however provide a reaction membrane having a number of test lines or zones each coated with at least one immobilized, capture binding member. In other words, the down-flow strips operate in absence of a source of first affinity mobilizable binding members located on the strip. In this way, most of the first affinity binding can occur off the strip.

The test result signal generator can group together a plurality of chromatographic testing strips (not shown). In addition, each strip, or a number of strips can be adapted to carry a number of test lines or zones which are adapted, such as providing each zone with a different sensitivity, to provide a measurable basis for a quantitative result display and/or adapted to provide a qualitative result display.

Referring now to FIGS. 2-6, the detailed operation of the porous dam structure will now be described.

Figure 2:
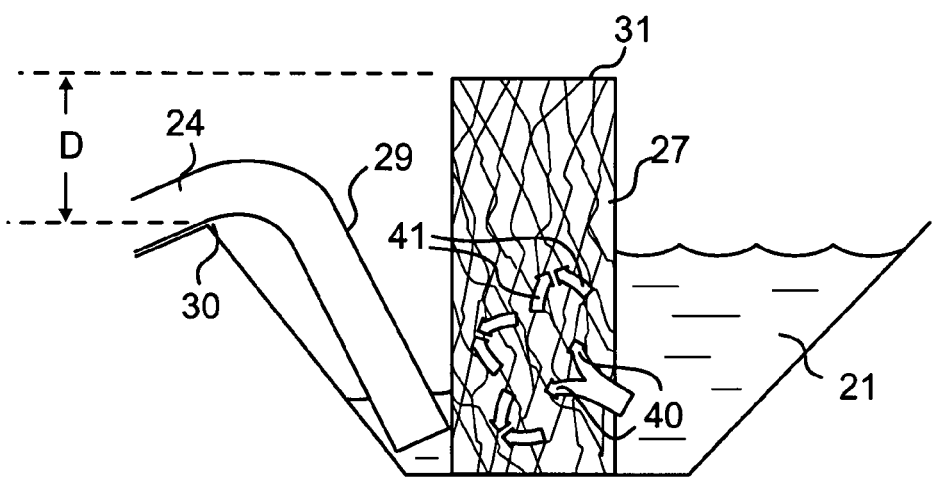
FIG. 2 is a diagrammatical view showing the fluid flow through the dam.

As shown in FIG. 2, the shape and dimensions of the pit 21, and the size and location of the dam 27 are further selected to avoid fluid flow over the top 31 of the dam. For example, the elevation of the top of the dam can be a distance D above the elevation of the escape port 30.

An important property of the dam 27 is that it is diffusive. The dam causes the flow to separate at the fluid front into a plurality of branches or furcations 40 which, when these furcations converge and join together again, do so from different directions. The convergence from different directions 41 causes a mixing of the entire specimen as it flows through. This mixing can cause the break-up of clumps of non-analyte molecules which may carry mobilizable labeled binding members, and/or clumps of the analyte itself and/or clumps of labeled analyte complexes which could carry additional mobilizable labeled binding members. The breaking up of these clumps help the to reduce the possibility of a false positive result. The mixing also reduces the differences in the concentrations of non-analyte molecules and labeled analyte complexes so that they are spread more evenly. Once the fluid passes through the dam, the concentrations have superior uniformity which leads directly to giving the labeled analyte complexes a greater opportunity to form the second affinity binding and thereby helping to reduce the possibility of a false negative result. In addition, the diffusive action of the porous dam 27 automatically further delays or interrupts the flow of the test fluids toward the reaction membrane 24 providing more incubation time for the first affinity binding to reach a maximum, thereby increasing the overall sensitivity and specificity of the test.

Figure 3:
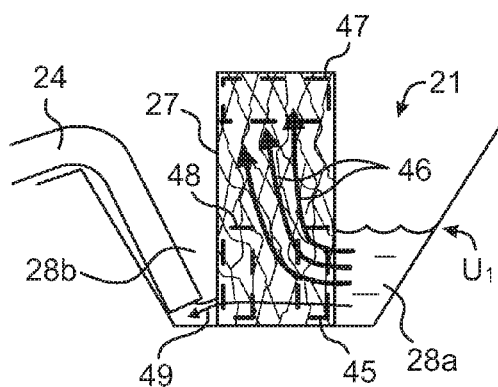
FIG. 3 is a diagrammatical cross-sectional side view of the reservoir area, showing the initial fluid flow into a dry dam.
Figure 4:
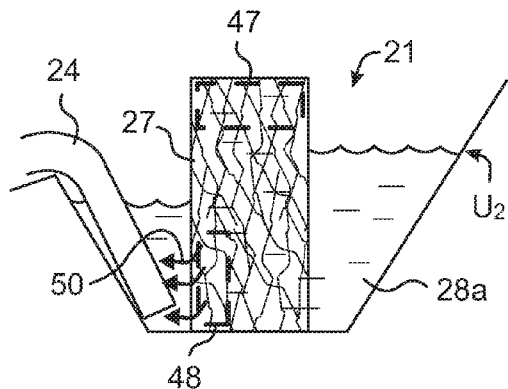
FIG. 4 is a diagrammatical cross-sectional side view of the reservoir area, showing the fluid flow out of a saturated dam.

As shown in FIGS. 3-4, another important property of the dam is that it diverts and traps the typically chemically disuniform initial fluid front.

Referring now to FIG. 3, the initial fluid flowing into the dam is driven primarily through capillary forces toward saturating the dam 27 before any substantial flow exits the dam. The initial fluid front enters the dam at a lower upstream entry portion 45 because of the low fluid level U1 in the upstream region 28a of the pit 21. From there, arrows 46 indicate that a predominant portion of the fluid in the initial fluid front will be diverted toward the dry, upper trap portion 47 of the dam rather than out of the lower downstream exit portion 48 and into the downstream region 28b of the pit 21 as indicted by the smaller flow arrow 49. In this way, a substantial amount of the typically chemically disuniform fluid front is diverted and trapped in the upper trap portion 47 of the dam. This initial fluid flow direction is enhanced by the differential surface tension caused by the surfactant treatment of the internal structures in the dam.

Referring now to FIG. 4, as the dam 27 eventually becomes saturated, the fluid pressure, due to the higher fluid level U2 in the upstream region 28a of the pit 21 and gravity, builds at the downstream side until the flow begins to exit as shown by arrows 50 from the lower downstream exit portion 48 creating a new fluid front having a more uniform chemistry as the first fluid entering the test membrane of the down-flow strip 24 which enhances the sensitivity and specificity. This relatively rapid breakdown of the surface tension barrier at the downstream side causes further mixing and leads to a more evenly mixed exiting fluid front. Because of the vertical structure of the diffusive dam 27, the initial fluid front generally stagnates at the top portion 47 of the dam while the fluid front exiting the dam is fluid from the more predictably mixed, non-initial-front fluids at the bottom of the dam.

In other words, the surfactant treated dam provides an additional, initial fluid front bypass function or a means for diverting the initial fluid front toward the top portion of the dam to become trapped rather than out the bottom portion as would be dictated by gravitational forces alone. As the dam becomes saturated with fluid and fluid pressure builds under the force of gravity, it exits the dam at a portion elevationally lower than the trapped fluid, thereby creating a new, more chemically uniform fluid front which flows into the reaction membrane, increasing accuracy.

It should be noted that the dam also acts as a reservoir for further delaying or interrupting the flow, giving more time for first affinity binding to occur. Depending on the chemistry of the test being performed and the viscosity of the sample being tested, the flow can be delayed between about 1 and about 40 seconds. For relatively low viscosity samples such as urine, the flow can be delayed for between about 2 and about 3 seconds.

As shown in FIGS. 5-8, another important property of the dam is that it is made of fiber material which through surface tension forces cause the branching and recombination of the initial fluid front from different directions to enhance mixing.

Figure 5:
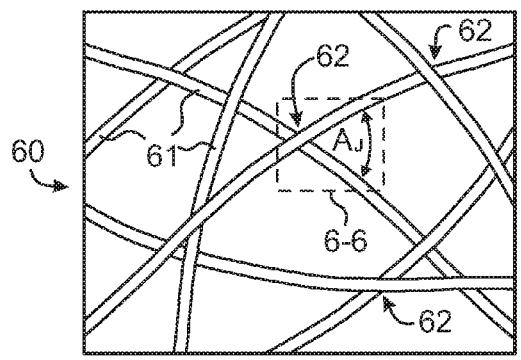
FIG. 5 is a diagrammatical microscopic illustration of fibers in a diffusive, flow interrupting structure.

As shown in FIG. 5, a portion 60 of a diffusive dam structure is made from relatively non-reactive, porous material such as glass fibers, cellulose, polysulfone, NYLON brand material, polyethylene, NOVYLON brand material, POREX CHEMISTRY K brand material, POREX CHEMISTRY A brand material, FILTRONA brand material, and the like, all commercially available. The material is selected to have intersecting surface structures such as fibers 61 oriented substantially differently to one another to create a plurality of junctions 62 where there is typically an angle $A_J$ formed between the two intersecting structures at their junction where the angle is not 0 degrees. In other words, at the junction, the fibers should not be substantially parallel so that they provide intersecting surfaces which, through surface tension forces cause the fluid to branch into furcations and converge causing a more thorough intermixing. It is important to note that the viscosity of the fluid can be a factor in determining the optimum density of fibers and hence the number of junctions required in a given volume of material. It has been found that glass fiber material commercially available from JBC of Elyria, Ohio provides an adequate number of junctions for many applications. Other non-fibrous porous materials can also be used that provide intersecting surface structures to cause fluid furcation and intermixing, and provide the capability for carrying a dried surfactant.

Figure 6:
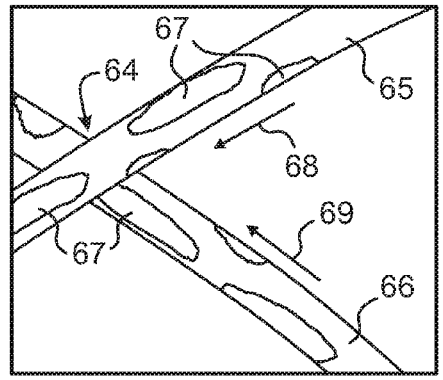
FIG. 6 is a diagrammatical microscopic close-up illustration of a fiber junction of a diffusive, flow interrupting structure of FIG. 5 taken at box 6-6.
Figure 7:
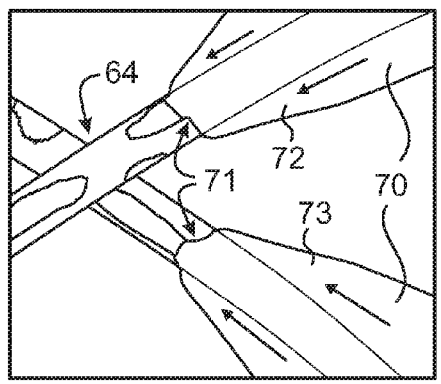
FIG. 7 is a diagrammatical microscopic illustration of the fiber junction of FIG. 6 where microscopic fluid flows are converging.
Figure 8:
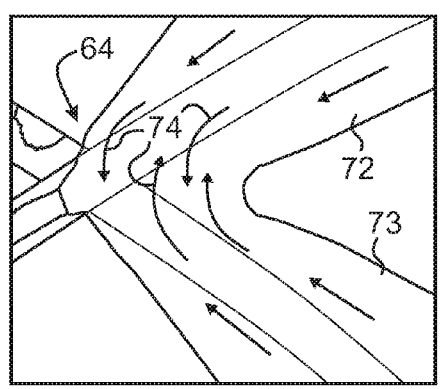
FIG. 8 is a diagrammatical microscopic illustration of the fiber junction of FIG. 6 where microscopic fluid flows have converged and mixed.

A portion of the diffusive dam structure can be pretreated with a surfactant by immersing the dam material during manufacturing into an amount of liquid surfactant so that it penetrates substantially all of the pores of the dam material. The dam material is then dried. This leaves a residue of the surfactant on the intersecting surface structures. As shown in FIG. 6, the junction 64 of two intersecting surface structures such as fibers 65,66 having dried surfactant residue 67 thereon creates two convergent fluid paths 68,69. As shown in FIG. 7, fluid 70 flowing through the dam will at its fluid front 71 have an affinity for separating into branches or furcations 72;73 which each tend to flow along the fluid paths formed by each surfactant treated fiber. As shown in FIG. 8, the furcations 72,73 will meet at the fiber junction 64 and their respective velocities will cause an intermixing as indicated by flow lines 74.

An exemplary surfactant is a detergent such as polyethylene glycol sorbitan monolaurate commercially available under the brand name TWEEN 20 from Sigma-Aldrich Corporation of St. Louis, Mo. Other detergents are acceptable such as TRITON X-100 brand, TRITON X-114 brand, TWEEN 80 brand, and sodium dodecyl sulfate ("SDS") detergents also available from Sigma-Aldrich Corporation. Depending on the test being conducted, other anionic, cationic, non-ionic and Zwitterionic detergents may also be acceptable.

Pretreatment of the dam can also be in the form of pH conditioning chemicals, and non-specific adhesive blocking molecules which will selectively filter, detach or "block-out" unwanted non-analyte adhesion molecules, typically proteins, which can non-specifically interfere and/or compete with the analyte in question in either or both of the first and second affinity binding stages of the test. Finally, another pretreatment condition can be no pretreatment in which case the pretreatment condition would be "unpretreated".

Referring now to FIGS. 9-10, there is shown a further embodiment of an immunoassay testing device 81. The device is packaged in a molded plastic enclosure 82 having an internal base pan 83. A retractable protective cover 84 is hingedly mounted at the back end 85 of the enclosure. The cover is in a closed position during storage and shipment of the device to protect a pair of operation buttons 86,87 from being inadvertently pressed, but can be flipped open for testing. The enclosure is shaped to have a generally planar bottom support surface 88 to support the device upon a level surface 89 so that a test station 90 holding one or more down-flow testing strips each having a reaction membrane 91 having test line zones 92, is oriented in an inclined position from the horizontal.

In the medial region of the device is a sample receiving well 96 having a funnel-shaped internal wall 97 and a filter screen 99 to help separate particles and adhesive matters from the fluid component of a specimen 98 such as whole blood or saliva. The sample receiving well 96 leads downwardly to a first, premix chamber 100 which receives the fluid component of the specimen in a first analytical part of the device. The specimen drops upon a conjugate pad 102 located on the floor 103 of the premix chamber thereby exposing the specimen to a source of mobilizable binding members conjugated to a label such as colloidal gold. The viscosity of blood or saliva for example generally prevents it from flowing on its own through to the rest of the device. The shape and dimensions of the first chamber can be adapted for other different viscosity fluid specimens.

The analytical testing reaction is initiated by opening a first tank 105 containing a self-contained, measured amount of mix buffer solution 106. The tank is formed by a generally inverted cup-like button structure 86 made from a durable, rigid, fluid impermeable material such as hard plastic and is slidingly built-in to the enclosure. The cup structure rim 108 is breakably thermo-sealed by a foil-plastic membrane 109. In its pretest position the mix buffer tank rests above a pair of puncturing pedestals 110 each having a plurality of prongs 111 extending upwardly from the pedestal upper surface 112. The prongs are located near the periphery of each pedestal to help cause fracturing of a pliable foil-plastic membrane. The tank is opened and the dispensing of its contents triggered by downward pushing manipulation 113 of the first button 86 which causes the tank to be lowered onto the pedestals, fracturing the foil-plastic membrane. This also increases the pressure of the solution to cause it to flow out of the fractures.

The mix buffer solution 106 is dispensed into the premix chamber 100 to contact the conjugate pad 102 and mix with the specimen to form a fluid mixture and initiate the first affinity binding reactions. In this way the premix chamber is subjectable to the mix buffer solution which can be characterized as a reactive solution. The button and openable tank forms a built-in, self-contained, user manipulable member for triggering the dispensing of the mix buffer solution onto the specimen. The amount or volume of mix buffer solution 106 is selected to adequately react with the amount of specimen. In this embodiment the volume of mix buffer is between about 200 and 300 microliters, and can be about 250 microliters.

Similarly to the previous embodiment, the mixture collects in a pit 123 formed into the floor 103 of the premix chamber 100. The pit is shaped and dimensioned to have a given capacity to form a temporary incubation reservoir behind a porous, diffusive dam structure 125. The mixture flows slowly and diffusively through the dam, primarily under the force of gravity alone, into one or more down-flow testing strips 91 held in a second chamber 126 in the test station 90. The flow of fluid continues under the combined effect of gravity, capillarity, and siphoning forces through the reaction membrane of the strips and eventually on to a flow absorbing pad 127 contacting the lower edge of the strips. The upper edge 128 of the strips extend into the pit 123 and contact the downstream side of the dam 125. A transparent window 129 sealed to the enclosure provides for direct viewing of the strips 91. A block of desiccant 130 is held in a third chamber 131 in the enclosure and is in communication with the absorbing pad through holes 132 to help extend shelf life. Additionally, another embodiment provides that the entire device is kept in a sealed hermetic aluminum plastic foil pouch bag until use.

The device also provides for a supply of a stop wash buffer solution 135 in order to stop the reaction in the strips and to carry away lingering chemicals and residue which could serve to obscure the lines formed in the zones 92 and also to remove any other non-specific materials from the reaction area. For example, one such stop wash buffer comprises: Tween 20: 1%; Glycerol: 0.5%; Glycine: 5-20 mM; and NaN3: 0.02% and the like.

The stop wash buffer solution 135 is contained in a second tank 136 located upstream from the premix chamber 100 and which is openable in a manner similar to the mix buffer tank 105 thereby providing a built-in, self-contained, user manipulable dispenser for releasing a measured volume of wash solution.

The wash buffer can be applied after a certain programmed waiting period which allows for the mixture to be drawn through the strips to an adequate degree. The waiting time can of course be dependent on the type of test being performed. For HIV detection the waiting period can be between about 0.5 and 2 minutes. The amount of wash buffer solution is selected to adequately wash the down-flow strips without unduly increasing the bulk of the device, and in this embodiment is between about 2 and 3 milliliters, and can be about 2.5 milliliters. In this embodiment the volume of wash buffer is about ten times that of the mix buffer. The flow of the stop wash buffer occurs relatively more quickly than the first flow of the mixture. The wash buffer, having about ten times the volume of the mixture, rapidly penetrates the already moistened dam and flushes out the non-specific binding caused by non-specific materials in the reaction area. This action helps to maximize the specificity of the present device to provide RCIT.

It is understood that both of the tanks 105,136 are in fluid flow communication with the channel 120 which is in fluid flow contact with the premix chamber 100 which is in fluid flow contact with the dam 125 which is in fluid flow contact with the strips 91, meaning there is a fluid path from the tanks, through the premix chamber 100, to the test station 90. However, as in previous embodiments, there is no uninterrupted fluid flow contact between the conjugate source and the reaction membrane, but rather the fluid must pass through the diffusive dam before reaching the reaction membrane.

It should also be noted that the device could include a second diffusive porous dam structure 137 spaced a distance apart of the first 125. In this way, the additional upstream diffusive dam 137 can have a different pretreatment condition than the downstream diffusive dam 125. For example, the upstream dam can be pretreated to have a pH conditioner; and the downstream dam be pretreated to have a non-specific adhesive blocking molecule and a surfactant. By splitting the pretreatment chemicals between two or more dams, the test device designer is not only given increased accuracy, but also more control and predictability over the reactions occurring at various stages of the testing process. Also, the designer is given the flexibility in assembly to inexpensively use the same housing design for a number of different tests depending on the type of dams, their pretreatment, the type of strips, the type of conjugate pad and buffer solutions which can easily be swapped. Also, using two or more pretreated dams potentially avoids manufacturing inconsistencies such as the second pretreatment chemical dislodging some of the first pretreatment chemical on a single dam.

It should be noted that in the multi-diffusive dam embodiments, no pretreatment can be a pretreatment condition. For example, the upstream dam 137 may simply be a glass fiber filter without any surfactant, pH conditioner or non-specific adhesive blocking molecule. In this case its pretreatment condition would be "unpretreated". This pretreatment condition would be different from the pretreatment condition of the downstream dam 125 which could have a dried surfactant pretreatment condition.

Again it should be noted that the increased accuracy provides the ability to make multi-line strips for detecting different analytes in a single specimen such as for detecting multiple major epitopes, i.e., antigenic determinants of an endogenious disorder such as AMI, or a single exogenous pathogen, or pathogenic organism such as bacteria, viruses such as HIV, parasites, rickettsia, and the like.

Figure 11:
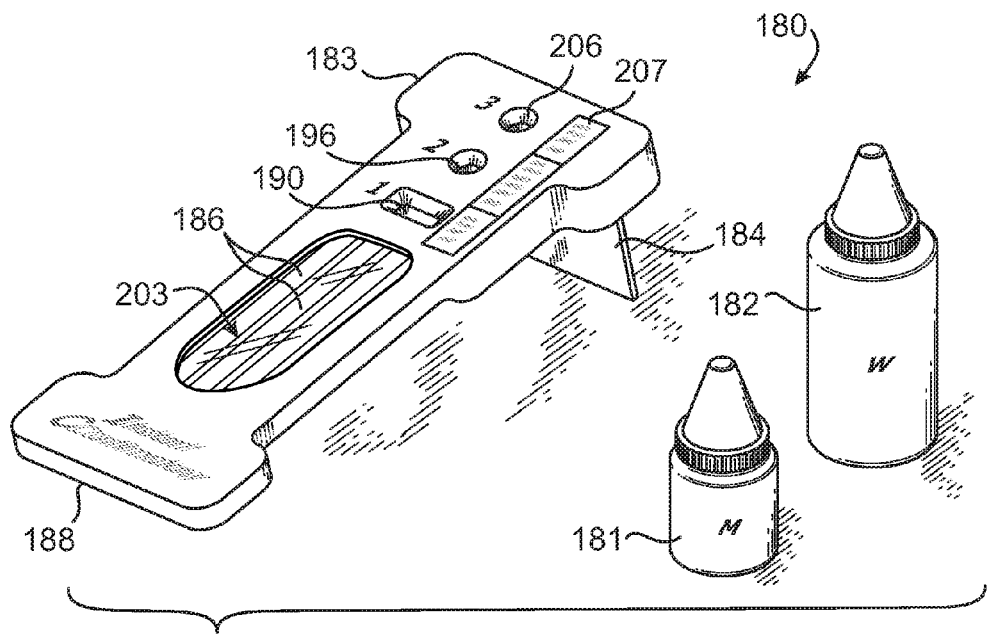
FIG. 11 is a perspective view of an alternate embodiment of the interrupted, diffusive gravity promoted downward flow testing device having buffer receiving wells and buffer containing dropper bottles.
Figure 12:
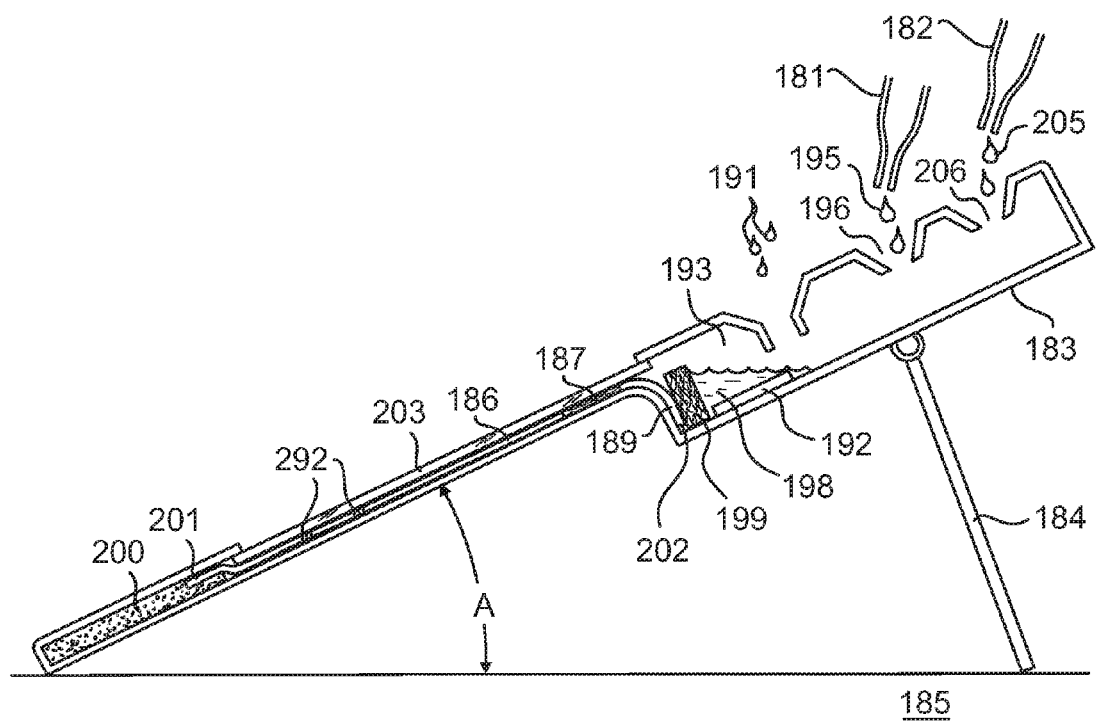
FIG. 12 is a diagrammatical cross-sectional side view of the device of FIG. 11.

Referring now to FIGS. 11 and 12, there is shown another alternate embodiment of an immunoassay testing device kit 180 which operates substantially similarly to the embodiment of FIG. 10 however a pair buffer-containing vials 181,182 replace the internal openable tanks. The present embodiment is thought to be less costly to manufacture. The kit includes a compact, molded plastic enclosure 183 having an extendable support leg 184 which in the open position orients the device at a favorably inclined angle A upon a level surface 185 so that one or more down-flow chromatographic strips 186 are oriented in an incline. The enclosure is sealed in a hermetic foil pouch (not shown) during storage and shipment to preserve and protect it and its internal chemicals, but is opened for testing. The enclosure also has a widened underside front surface portion 188 to provide greater stability.

A sample receiving well 190 is provided on the medial region of the enclosure upstream from the strips 186 to accept the fluid specimen 191 which drops upon a conjugate pad 192 located on the floor of a premix chamber 193. The test is initiated by dispensing from a first dispenser or vial 181 a measured amount of mix buffer solution 195 into a first mix buffer receiving well 196. The mix buffer solution flows down toward the premix chamber 193 to contact the conjugate pad 192 and mix with the specimen to form a fluid mixture and initiate the first affinity binding reactions. Similarly to the previous embodiments, the premix chamber is therefore subjectable to the mix buffer solution which can be characterized as a reactive solution. The amount or volume of mix buffer solution is selected to adequately react with the amount of specimen. In this embodiment the volume of mix buffer is typically between about 200 and 300 microliters, and can be about 250 microliters.

Similarly to the previous embodiment, the mixture collects in an incubation pit 198 behind a porous, diffusive dam structure 199, then flows diffusively under primarily the force of gravity alone through the dam and into one or more down-flow testing strips 186. Flow continues through the strips under the combined effect of gravity, capillarity, and siphoning forces and eventually collects in an absorbing pad 200 contacting the strips at its downstream edge 201. The upstream edge 202 of the strips extend into the pit 198 and contact the downstream side of the dam 199. A transparent window 203 sealed to the enclosure provides for direct viewing of the strips 186.

Further, the down-flow strips can be adapted to carry a fluid-diffusing pad 187 to more thoroughly mix the fluid between the strip's top end 189 and the test result signal generating zones 292. The pad is made from a single layer of uniformly dispersed porous matrix material such as uniformly porous polyethylene commercially available from Porex Corporation of Fairburn, Georgia.

A supply of wash buffer solution 205 can be dispensed from the wash buffer dispenser or vial 182 into a second, wash buffer receiving well 206 and on to the down-flow strips. The function of the wash buffer is the same as in prior embodiments.

It will be clear to those skilled in the art that the premeasured vials described above may be replaced with a single vial or even a large volume bottle having enough solution for conducting a number of tests where the user is expected to dispense the proper amount of buffer solution at the proper time. The buffer vial or vials therefore act as a user manipulatable dispenser for dispensing the buffer solution. Alternately, a single buffer receiving well can be used rather than separate mix and wash buffer wells. Providing the additional wells helps the user keep track of the steps that have been performed and provides additional space on the top surface of the enclosure to provide a convenient placard 207 for carrying test instructions.

Figure 13:
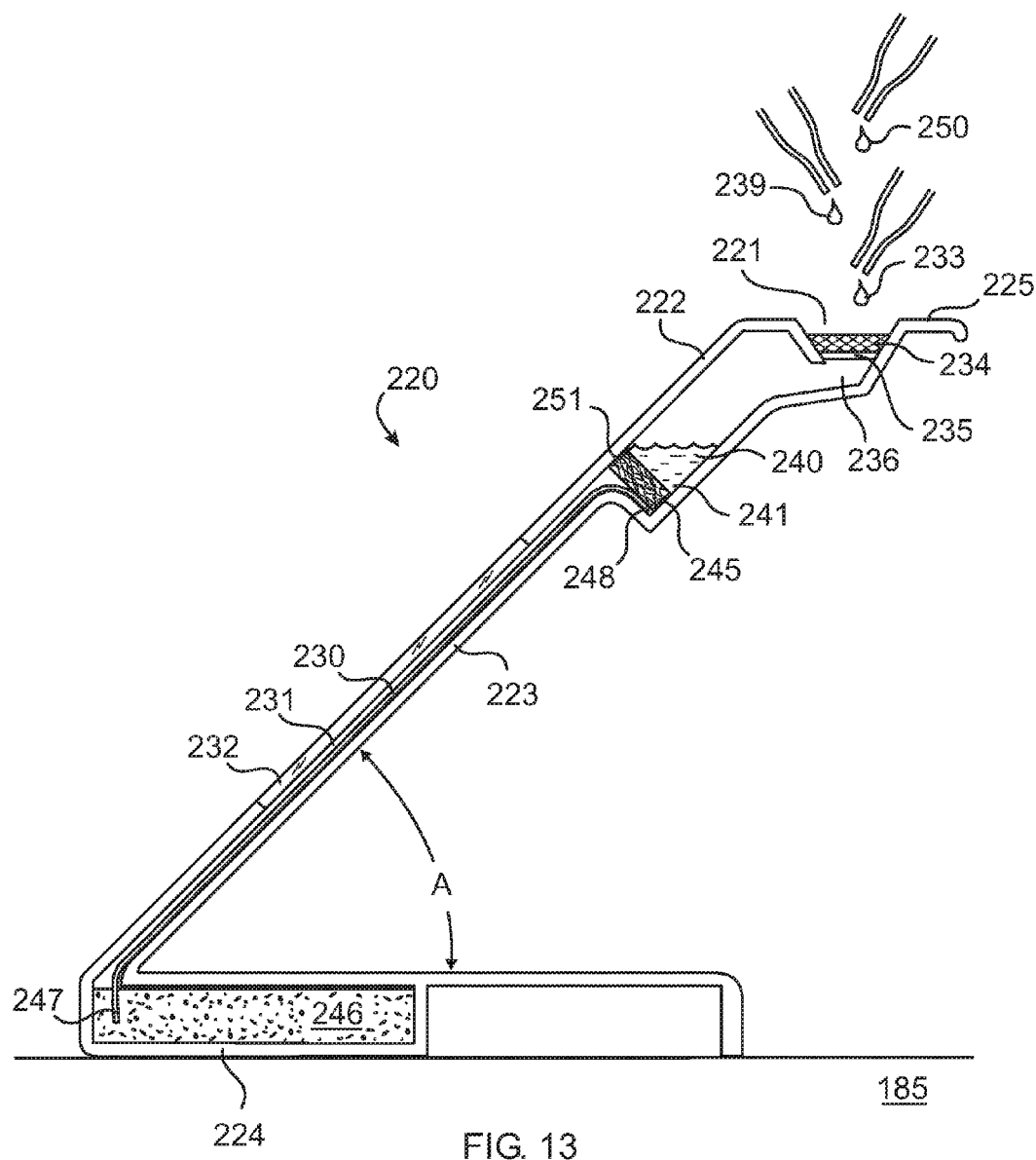
FIG. 13 is a diagrammatical cross-sectional side view of an alternate embodiment of the interrupted, diffusive downward flow testing device having a single sample and buffer receiving well.

Referring now to FIG. 13, there is shown another alternate embodiment of an immunoassay testing device 220 which operates substantially similarly to the embodiment of FIGS. 11-12 however a single fluid receiving well 221 replaces the multiple receiving wells of that embodiment. The present embodiment is thought to be less costly to manufacture. The device includes a compact, molded plastic enclosure 222 shaped and dimensioned to rest upon a level surface 185. The enclosure has a platform 223 extending at a non-vertical, non-horizontal angle A from a substantially horizontal base 224 to a substantially horizontal upper deck 225. The deck being substantially horizontal provides for a clear, large target receiving well for users depositing fluid therein given the overall size of the deck. The slanted platform carries at least one down-flow strip 230 in a second chamber 231 behind a transparent viewing window 232. The entire enclosure is sleek enough to be readily sealed in a hermetic foil pouch (not shown) during storage and shipment.

The fluid receiving well 221 is provided on the deck 225 upstream from the strip 230 to accept the fluid specimen 233 which drops through a filter screen 234 and onto a conjugate pad 235 located on the floor of a premix chamber 236. A measured amount of mix buffer solution 239 is then dispensed into the well 221. The mix buffer solution combines with the specimen and mobilzable labeled binding members provided by the conjugate pad 235 to form a fluid mixture and initiate the first affinity binding reactions. The mixture 240 collects in an incubation pit 241 before flowing through a diffusive dam structure 245 and on, under the combined effect of gravity, capillarity, and siphoning forces, to the strip 230 and eventually collects in an absorbing pad 246 contacting the strip at its downstream edge 247. The upstream edge 248 of the strip extends into the pit 241 and contacts the downstream side of the dam 245. A supply of wash buffer solution 250 is then dispensed into the receiving well 221 and on to the down-flow strips. The function of the wash buffer is the same as in prior embodiments. The shape and dimensions of the pit 241, and the size and location of the dam 245 are further selected to avoid fluid flow over the top of the dam. An example is selecting the top of the dam to contact 251 the upper wall of the enclosure.

The interrupted, diffused, down-flow test can rapidly provide an analytical panel or profile of antigen or antibody detection, and confirm the biochemical or pathogenic condition such as HIV infection, or early stage cancer prior to metastasis, or acute cardiac disorder by way of a simple, inexpensive and disposable device that can be manipulated safely by a relatively low skilled person. The quality of the clinical performance of this novel platform technology surpasses previous rapid testing technologies, such as Latex particle agglutination, Flow-Through test, and the currently wide-spread Lateral Flow devices. It is a technology of Rapid Confirmatory Immunological Testing (RCIT).

Depending on the disease being tested and the condition of the fluid specimen, many of the above embodiments have been found to achieve an accuracy of at least 99.9%.

While the exemplary embodiments have been described, modifications can be made and other embodiments may be devised without departing from the spirit of the invention and the scope of the appended claims.

What is claimed is:

1. A flow immunoassay device for testing a fluid specimen for the presence of an analyte, wherein said device comprises:
    a first chamber shaped and dimensioned to accept said specimen and be subjectable to a source of a mobilizable labeled binding member bindable to said analyte;
    a second chamber holding at least one test result signal generator responsive to an amount of said analyte bound to said labeled binding member; and,
    a flow interrupting formation located on a fluid path between said first and second chambers;
    wherein said flow interrupting formation comprises:
        a first porous diffusive structure comprising;
            a lower upstream entry portion;
            an upper trap portion; and,
            a lower downstream exit portion;
    wherein said fluid flows to said flow interrupting formation primarily under the force of gravity alone;
    wherein an initial fluid front of said fluid said entry portion is automatically diverted upwardly primarily under the force of capillarity alone and against the force of gravity into said trap portion;
    wherein said fluid flows through said generator primarily under the combined forces of gravity, siphoning and capillarity; and,
    whereby a first affinity binding reaction between said analyte and said labeled binding member is substantially completed before said fluid enters said second chamber.

2. The device of claim 1, which further comprises:
    said initial fluid front having a greater chemical disuniformity than an exiting fluid front exiting said structure.

3. The device of claim 1, wherein said first structure has a first pretreatment condition.

4. The device of claim 3, wherein said first pretreatment condition is selected from the group consisting of: being pretreated with a surfactant; being pretreated with a pH conditioner, being pretreated with a non-specific adhesive blocking molecule, and having no pretreatment.

5. The device of claim 1, wherein said device further comprises a second mixing, diffusing and filtering structure, wherein said first structure has a first pretreatment condition and said second structure has a second pretreatment condition, and wherein said first pretreatment condition is different from said second pretreatment condition.

6. The device of claim 1, wherein said first structure is shaped and dimensioned to have a trap portion at an elevation higher than fluid entry and exit portions.

7. The device of claim 1, wherein said first structure comprises a material selected from the group consisting of: glass fiber, cellulose and fibrous plastic.

8. The device of claim 1, wherein there is no direct fluid flow contact between said source and said generator without passing through said flow interrupting formation.

9. The device of claim 1, wherein said first porous diffusive structure comprises means for diverting an initial fluid front passing therethrough.

10. The device of claim 1, wherein said device further comprises:
    said first porous diffusive structure comprising a first material having a plurality of fibers oriented substantially differently to one another and branching into furcations and convergences.

11. The device of claim 1, wherein said generator comprises a chromatographic test strip including a reaction membrane oriented in an oblique, downward flow orientation, said membrane having at least one test zone.

12. The device of claim 11, wherein said strip is formed without a source of mobilizable labeled binding members.

13. The device of claim 1, wherein said generator comprises a plurality of test zones adapted to provide a measurable basis for a quantitative result display.

14. The device of claim 1, which further comprises means for dispensing a supply of mix buffer solution into said first chamber.

15. The device of claim 1, wherein said device is formed in absence of a pump built into said device.

16. The device of claim 1, which further comprises a user manipulatable dispenser shaped and dimensioned to releasably hold a supply of a mix buffer solution, wherein said dispenser in an open condition is in fluid communication with said flow interrupting formation.

17. The device of claim 16, wherein said supply of mix buffer solution has a volume between about 200 microliters and about 300 microliters.

18. The device of claim 17, which further comprises a second supply of wash buffer solution having a volume between about 2.5 milliliters and about 3 milliliters.

19. The device of claim 1, wherein said formation comprises a flow delaying reservoir separated into first and second zones by a first porous structure.

20. The device of claim 1, wherein a second affinity binding reaction occurs in absence of any substantial continuation of said first affinity binding reaction.

* * * * *